US006288030B1

(12) United States Patent
Hershenson

(10) Patent No.: US 6,288,030 B1
(45) Date of Patent: Sep. 11, 2001

(54) STEM CELL FACTOR FORMULATIONS AND METHODS

(75) Inventor: Susan I. Hershenson, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 08/172,507

(22) Filed: Dec. 22, 1993

(51) Int. Cl.$^7$ .......................... A61K 38/00; A61K 38/24; C07K 1/00
(52) U.S. Cl. .............. 514/12; 514/21; 530/350; 530/399
(58) Field of Search .............. 514/12, 21; 530/350, 530/399

(56) References Cited

U.S. PATENT DOCUMENTS

| | | | |
|---|---|---|---|
| 4,877,608 | * 10/1989 | Lee et al. | 424/176.1 |
| 5,192,743 | 3/1993 | Hsu et al. | 514/8 |

FOREIGN PATENT DOCUMENTS

| | | | |
|---|---|---|---|
| 2014009 | * 10/1990 | (CA) | . |
| 0 308 238 | 3/1989 | (EP) | . |
| 0314095 | * 5/1989 | (EP) | . |
| 0 423 980 | 4/1991 | (EP) | . |
| 55034001 | * 8/1978 | (WO) | . |
| 82/21599 | * 12/1982 | (WO) | . |
| 9012029 | * 10/1990 | (WO) | . |
| WO 91/05795 | 5/1991 | (WO) | . |
| WO91/05795 | * 5/1991 | (WO) | . |
| WO 92/00376 | 1/1992 | (WO) | . |
| WO9312812 | * 7/1993 | (WO) | . |
| WO94/07510 | * 4/1994 | (WO) | . |

OTHER PUBLICATIONS

Hora, et al. Developments in Biological Standardization, vol. 74, Karger, Basel, (1992).
Laemmli, Nature 227: 680–685 (1970).
Seguro, Cryobiology 27: 70–79 (1990).

* cited by examiner

*Primary Examiner*—Sean McGarry
*Assistant Examiner*—Karen A. Lacourciere
(74) *Attorney, Agent, or Firm*—Matthew W. Knight; Ron K. Levy; Steve M. Odre

(57) ABSTRACT

The present invention relates to lyophilized formulations of Stem Cell Factor (SCF) with increased stability. The formulations of lyophilized SCF include amino acid buffers and sucrose. Methods of producing said formulations are also disclosed in the specification.

13 Claims, 7 Drawing Sheets

Figure 1:
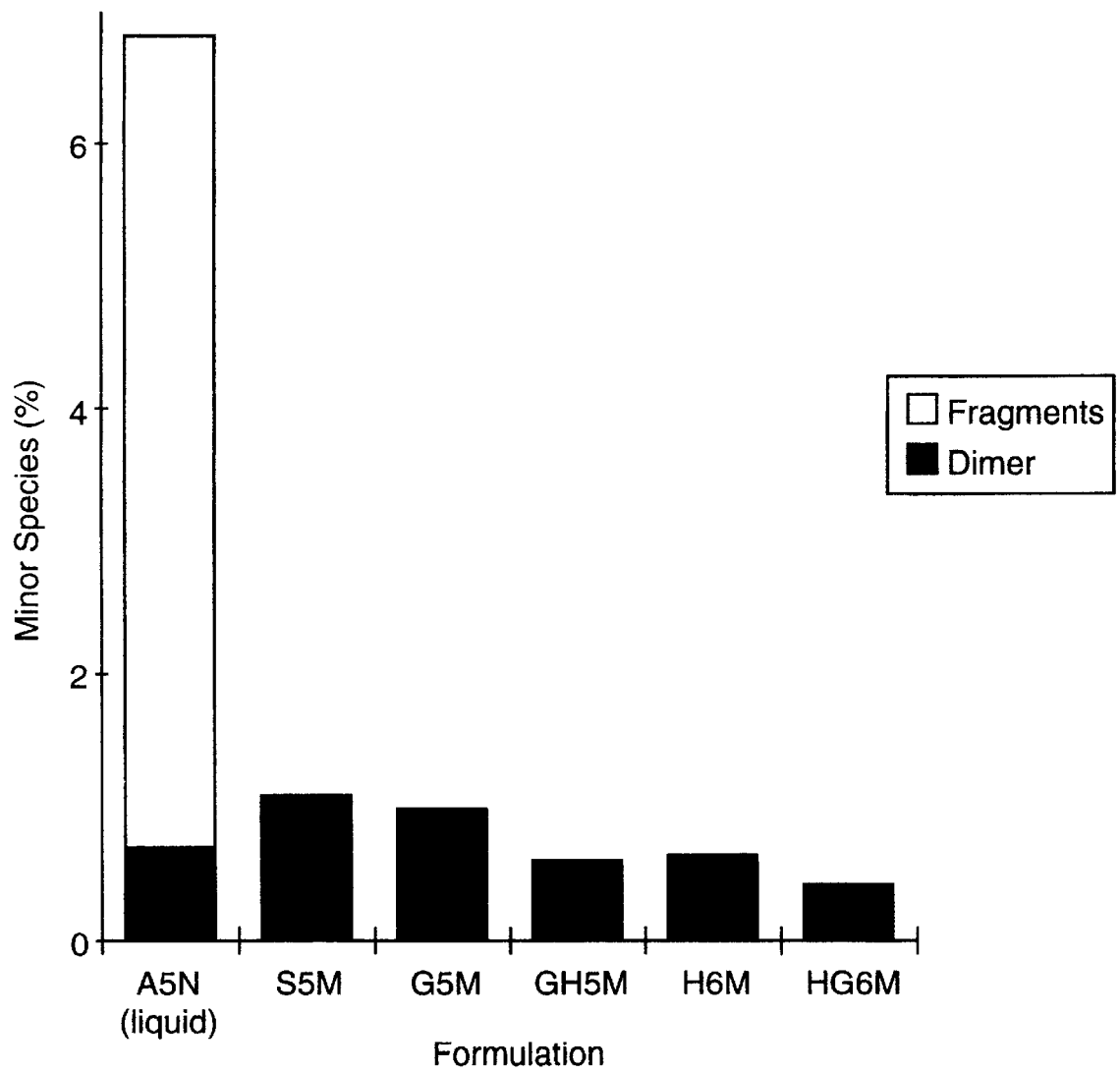

| Lane No. | Sample |
|---|---|
| 1 | MW markers |
| 2 | Blank |
| 3 | SCF standard |
| 4 | Blank |
| 5 | A5N (liquid formulation control) |
| 6 | HG6M |
| 7 | K6M |
| 8 | K6SuM |
| 9 | K6SuPM |

| Lane No. | Sample |
|---|---|
| 1 | MW markers |
| 2 | |
| 3 | SCF standard |
| 4 | A5N (liquid control) |
| 5 | HG6M |
| 6 | HG6PM |
| 7 | HG6SuM |
| 8 | HG6SuPM |
| 9 | K6M |
| 10 | K6PM |
| 11 | K6SuM |
| 12 | K6SuPM |

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 501 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
ATGGAAGGTA TCTGCCGTAA CCGTGTTACT AACAACGTTA AAGACGTTAC TAAACTGGTT      60

GCTAACCTGC CGAAAGACTA CATGATCACC CTGAAATACG TTCCGGGTAT GGACGTTCTG     120

CCGTCTCACT GCTGGATCTC TGAAATGGTT GTTCAGCTGT CTGACTCTCT GACTGACCTG     180
```

-continued

```
CTGGACAAAT TCTCTAACAT CTCTGAAGGT CTGTCTAACT ACTCTATCAT CGACAAACTG      240

GTTAACATCG TTGACGACCT GGTTGAATGC GTTAAAGAAA ACTCTTCTAA AGACCTGAAA      300

AAATCTTTCA AATCTCCGGA ACCGCGTCTG TTCACTCCGG AAGAATTCTT CCGTATCTTC      360

AACCGTTCCA TCGACGCTTT CAAAGACTTC GTTGTTGCTT CCGAAACCTC CGACTGCGTT      420

GTTTCCTCCA CCCTGTCTCC GGAAAAAGAC TCCCGTGTTT CGGTTACCAA ACCGTTCATG      480

CTGCCGCCGG TTGCTGCTTA A                                                501
```

(2) INFORMATION FOR SEQ ID NO:2:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Glu Gly Ile Cys Arg Asn Arg Val Thr Asn Asn Val Lys Asp Val
1               5                   10                  15

Thr Lys Leu Val Ala Asn Leu Pro Lys Asp Tyr Met Ile Thr Leu Lys
            20                  25                  30

Tyr Val Pro Gly Met Asp Val Leu Pro Ser His Cys Trp Ile Ser Glu
        35                  40                  45

Met Val Val Gln Leu Ser Asp Ser Leu Thr Asp Leu Leu Asp Lys Phe
    50                  55                  60

Ser Asn Ile Ser Glu Gly Leu Ser Asn Tyr Ser Ile Ile Asp Lys Leu
65                  70                  75                  80

Val Asn Ile Val Asp Asp Leu Val Glu Cys Val Lys Glu Asn Ser Ser
                85                  90                  95

Lys Asp Leu Lys Lys Ser Phe Lys Ser Pro Glu Pro Arg Leu Phe Thr
            100                 105                 110

Pro Glu Glu Phe Phe Arg Ile Phe Asn Arg Ser Ile Asp Ala Phe Lys
        115                 120                 125

Asp Phe Val Val Ala Ser Glu Thr Ser Asp Cys Val Val Ser Ser Thr
    130                 135                 140

Leu Ser Pro Glu Lys Asp Ser Arg Val Ser Val Thr Lys Pro Phe Met
145                 150                 155                 160

Leu Pro Pro Val Ala Ala
                165
```

STEM CELL FACTOR FORMULATIONS AND METHODS

FIELD OF THE INVENTION

The present invention relates to novel stem cell factor compositions and methods. More specifically, the present invention relates to novel lyophilized formulations of stem cell factor and methods for production.

BACKGROUND

Stem cell factor ("SCF") is an early acting hematopoietic factor. See PCT WO 91/05795, entitled "Stem Cell Factor," herein incorporated by reference. SCF pharmaceutical compositions are known in the art, PCT WO 91/05795, supra, pages 20–21, however, an SCF pharmaceutical composition with increased shelf-life would be beneficial to both producers and consumers of the product.

In solution, SCF stability is limited by a number of degradation reactions, including cleavage, deamidation, and modification on RP-HPLC. Freeze drying (lyophilization) is considered useful and effective for preservation of many biologically active materials, including proteins. However, lyophilization induces its own stresses, including extreme concentration of the protein during the freezing process and removal of water, which may result in instability of the product. Hence, lyophilization may result in increased rates of crosslinking (covalent oligomer formation) and noncovalent aggregation, in addition to deamidation and oxidation, both of which can occur in the lyophilized state as well as the liquid state. Thus protective agents are often required to enhance stability of the drug by a number of mechanisms, including raising the glass transition of the formulation (that is, the temperature at which the composition changes from a fluid, rubbery and reactive state to a rigid, and, therefore less reactive state); acting as cryo- or lyoprotectants, (that is protective agents during the freezing and/or drying processes); and/or by replacing bound water molecules that are necessary for the conformational stability of the protein.

Amino acids have been noted in some cases to act as stabilizers for freeze-dried protein products. Sodium glutamate and lysine-HC1 have been reported to have cryoprotective effects on the freeze denaturation of a protein, lactate dehydrogenase (Seguro, et al., Cryobiology 27; 70–79 (1990)). Hora, et al. report the use of the L-arginine, L-carnitine chloride, or L-betaine as buffers for rhIL-2 (in Developments in Biological Standardization, Vol. 74, Karger, Basel, 1992). The formulations buffered with betaine showed dimer formation in accelerated testing, while arginine/carnitine-buffered formulations showed poor mechanical stability, leading to aggregation of the protein during production. Thus, the use of amino acids does not predictably enhance stability of lyophilized protein products.

Additionally, incorporation of small amounts of salt may, in some cases, destabilize lyophilized products, including proteins. The salts may be introduced during the pH adjustment of the formulation by addition of strong acids or bases. At the very low concentrations present in such a case, the salt may be trapped in the amorphous phase with the protein and may decrease the glass transition of the formulation or otherwise exert a detrimental effect on the stability of the protein drug. Elimination of such salt may therefore be desirable. Other classes of molecules, including mono- and di-saccharides, and polymers such as PVP have also been reported as stabilizers of lyophilized proteins, but, again, their utility is not predictable for any given protein product.

SUMMARY OF THE INVENTION

The present invention relates to novel formulations of freeze dried SCF which include amino acid buffers. Surprisingly, incorporation of the amino acids histidine and/or glutamic acid as buffers increases SCF stability, as compared to formulations in which inorganic or other types of organic compounds are used to adjust pH. Preferred forms of the present formulations are those in which pH is adjusted by combining histidine and glutamic acid. Adjusting pH by this method avoids the need to titrate with strong acid or base, which creates salts. The present formulations may optionally include additional stabilizers such as sucrose. Such formulations may also optionally include a bulking agent, and/or an osmolarity regulating agent, such as mannitol.

The protective effect of the present amino acid buffer is observed, but the precise mode of action is unknown. One possible explanation relates to the glass transition temperature for histidine. Essentially, the glass transition temperature is that temperature at which the composition (here, containing SCF) changes from being a relatively inflexible, unreactive (and therefore fairly stable) state to a relatively flexible, more reactive (and therefore less stable) state. Because the glass transition temperature of histidine is relatively high compared to non-amino acid buffer components, histidine may contribute to the overall stability of the freeze-dried formulation.

Another mechanism by which amino acids may protect SCF is by co-concentrating with the protein during freezing, thus serving to dilute and protect the protein. It is also possible that the amphiphilic amino acids may specifically interact with the protein to protect it against denaturaturation during the freezing and/or freeze drying processes.

In another aspect of the present invention, sucrose is seen to have a protective effect on lyophilized SCF formulations. Again, the precise mode of action is unknown, but one possible explanation relates to the glass transition temperature, similar to the explanation set forth above for histidine. The glass transition temperature overall depends on the glass transition temperature of the formulation components, as well as their relative proportions, and sucrose also has a relatively high glass transition temperature. Because sucrose co-concentrates with SCF in the frozen state, it may serve to dilute the SCF, and therefore protect against aggregation.

An alternative explanation relates to water replacement. Proteins such as SCF contain bound water molecules, the replacement of which by polyols may increase stability. Sucrose may have superior water replacement properties over other polyols.

The present formulations, using the amino acid histidine and/or the amino acid glutamic acid, and optionally sucrose, and optionally a bulking agent such as mannitol, and further optionally an osmolarity regulating agent, which also may be mannitol, satisfy a need for an SCF formulation with increased stability. The present invention also relates to methods for preparation of such formulations.

DETAILED DESCRIPTION OF THE DRAWINGS

FIG. 1 is a bar graph illustrating the relative stability, in terms of the increase in minor SCF species (fragments being indicated by outline, dimers indicated by blackened-in outline), of various formulations of SCFmet1-165 (at a concentration of 6.0 mg/mL) in an accelerated stability study conducted at high temperature (45° C.) for four weeks.

In formulations without amino acids, or with only one amino acid in the buffer, the pH was adjusted with addition of strong acid or base. The first bar (on the left) represents a liquid solution of SCFmet1-165 containing 10 mM sodium acetate, pH 5.0, and 140 mM NaCl (A5N). The second bar (S5M) represents 10 mM sodium succinate, pH 5.0, 5% mannitol; the third bar (G5M) represents 10 mM glutamic acid, pH 5.0, 5% mannitol; the fourth bar (GH5M) is 10 mM glutamic acid, 8.35 mM histidine pH 5.0, 5% mannitol; the fifth bar (H6M) represents 10 mM histidine pH 6.0, 5% mannitol; and the sixth bar (HG6M) represents 10 mM histidine, 5 mM glutamic acid, pH 6.0, 5% mannitol. This Figure illustrates that samples buffered with glutamic acid or histidine are more stable than a comparable formulation buffered with a non-amino acid (succinate); and that formulations buffered with a combination of histidine and glutamic acid contain less crosslinked dimer than formulations of the same pH buffered with a single amino acid.

Figure 2:
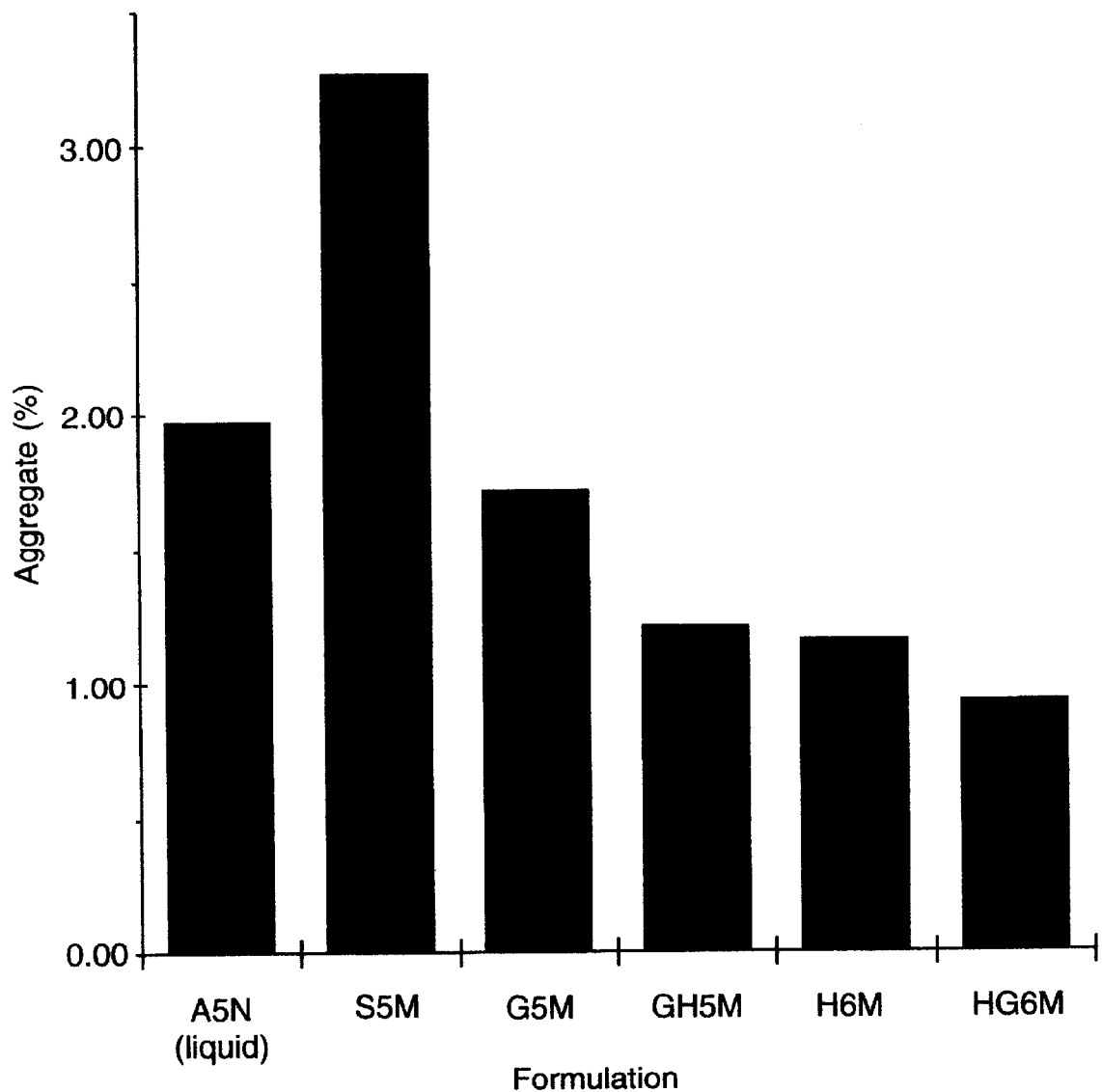

FIG. 2 is a bar graph illustrating the relative stability, in terms of aggregation (which may include crosslinked and non-crosslinked species) of various formulations of SCFmet1-165. The samples and conditions were the same as those of FIG. 1.

Figure 3:
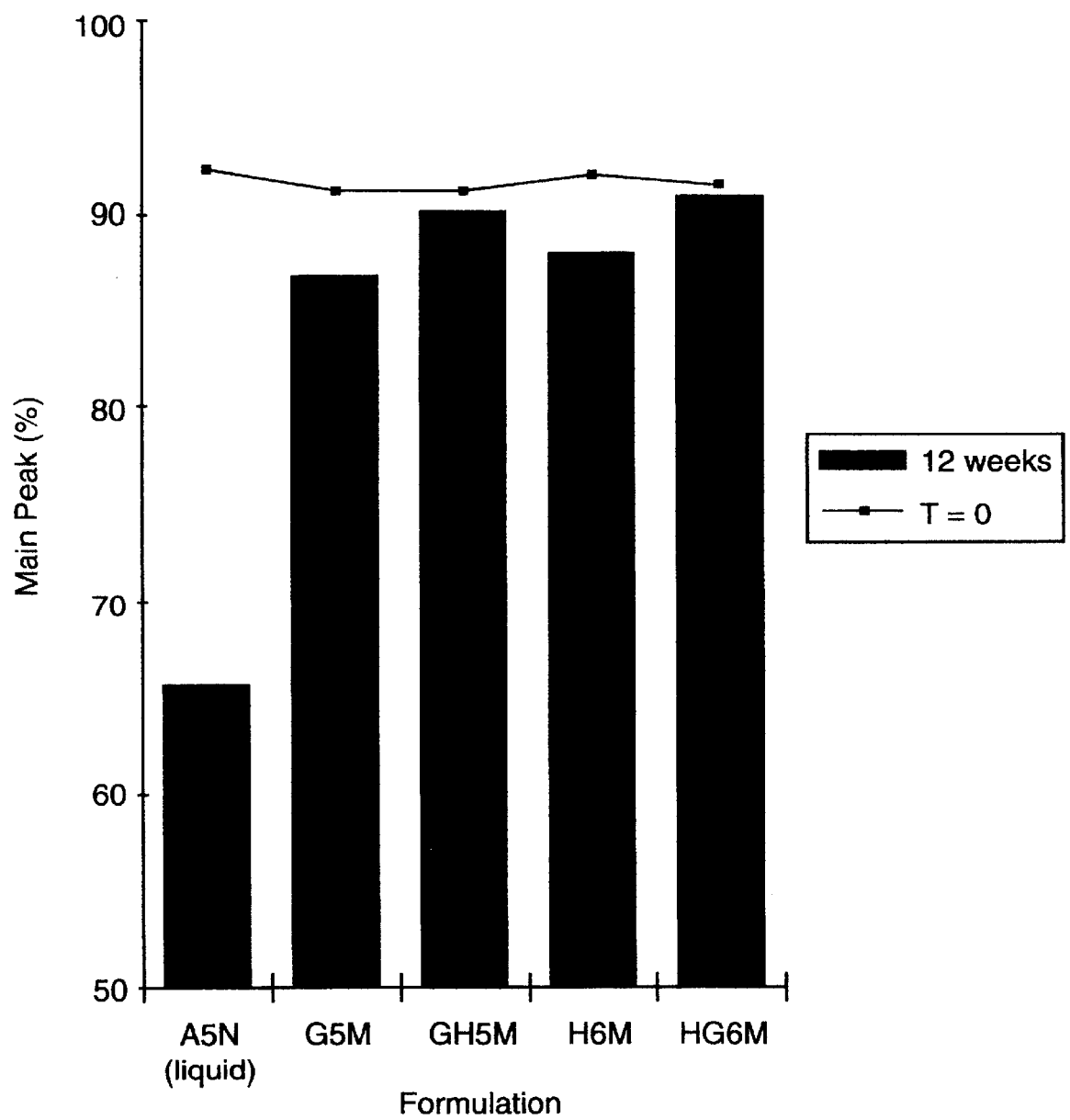

FIG. 3 is a bar graph illustrating the relative purity, in terms of species detectable by RP-HPLC, of various formulations of SCFmet1-165, in an accelerated stability study conducted at high temperature (45° C.) for 12 weeks. The samples shown are the same as those of FIG. 1, except that the sample without an amino acid buffer is deleted from this Figure. The points at the top of the Figure, indicated by small boxes, indicates the purity of the samples at the beginning of the study.

Figure 4:
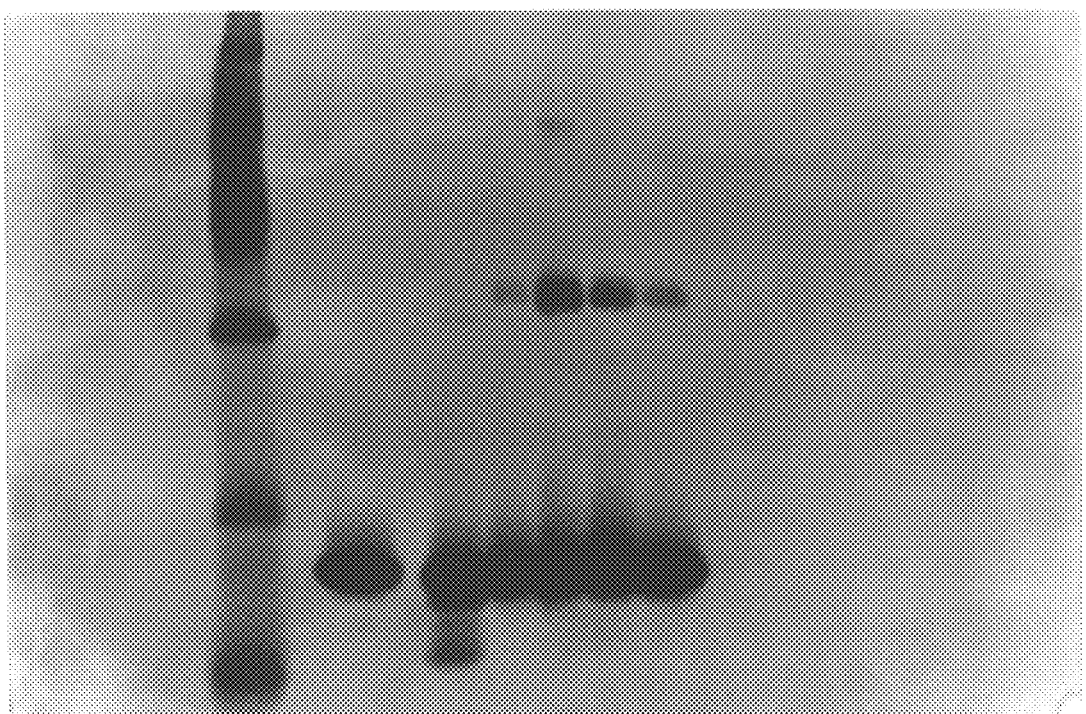

FIG. 4 is a photograph of a silver-stained SDS gel showing the degree of crosslinking occurring in various SCFmet1-165 formulations after incubation for four weeks at 45° C. Lane 1 (from the left) is molecular weight markers, lane 2 is blank; lane 3 is an SCFmet1-165 standard; lane 4 is blank; lane 5 is a liquid formulation SCFmet1-165 control (A5N described as in FIG. 1 except at 1.5 mg/mL); lane 6 is HG6M described for FIG. 1 (except containing SCF at 1.5 mg/mL); lane 7 (K6M) is an SCFmet1-165 1.5 mg/mL formulation containing 10 mM K phosphate, pH 6.0, 5% mannitol; lane 8 is an SCFmet1-165 1.5 mg/mL formulation containing 10 mM K phosphate pH 6.0, 0.5% sucrose, 4.5% mannitol (K6SuM); lane 9 is an SCFmet1-165 1.5 mg/mL formulation containing 10 mM K phosphate, pH 6.0, 0.5% sucrose, 0.5% polyethylene glycol-8000, and 4.5% mannitol (K6SuPM).

Figure 5:
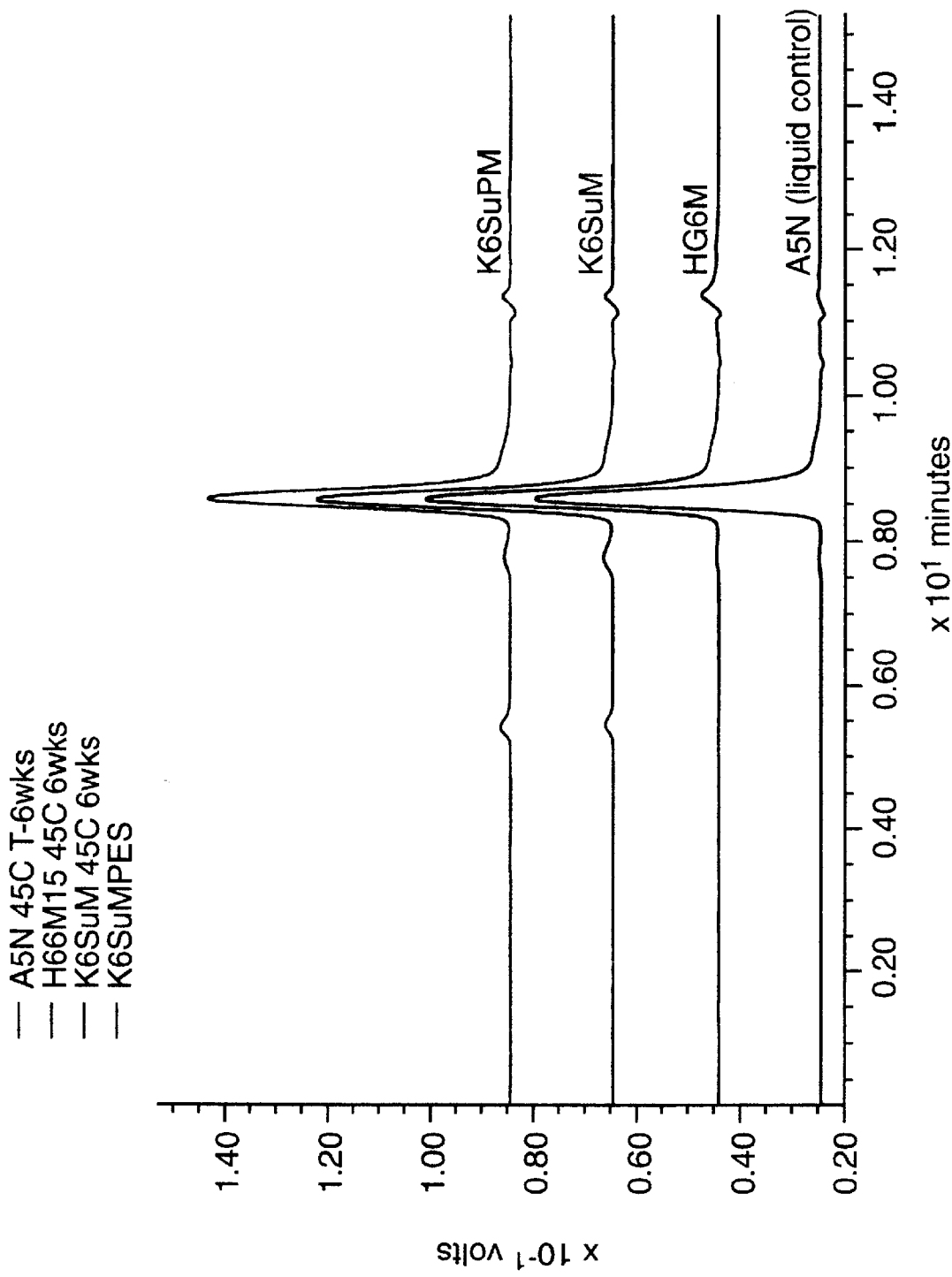

FIG. 5 is an SEC-HPLC chromatogram of various SCF formulations after six weeks of incubation at (45° C.). The samples used are those described above for FIG. 4.

Figure 6:
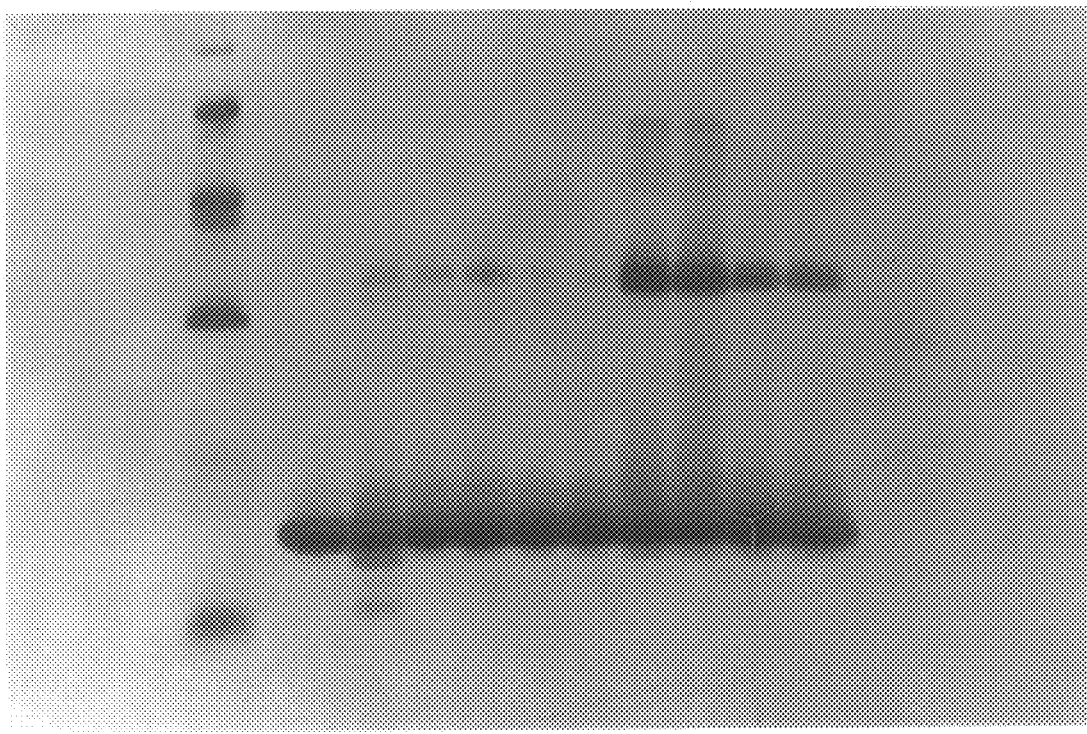

FIG. 6 is a photograph of a silver-stained SDS gel of various SCFmet1-165 (1.5 mg/mL) formulations after five weeks of incubation at 45° C. The formulations, unless otherwise indicated, are as described for FIG. 4. Lane 1 (from the left) is molecular weight markers; lane 2 is blank, lane 3 is an SCFmet1-165 standard; lane 4 is A5N (SCF liquid control); lane 5 is HG6M; lane 6 (HG6PM) is an SCFmet1-165 formulation containing 10 mM histidine, 5mM glutamic acid, pH 6.0, 0.5% PEG-8000, and 5% mannitol; lane 7 (HG6SuM) is an SCFmet1-165 formulation containing 10 mM histidine, 5 mM glutamic acid, pH 6.0, 0.5% sucrose and 4.5% mannitol; lane 8 (HG6SuPM) is an SCFmet1-165 formulation containing the same as HG6SuM with the addition of 0.5% polyethylene glycol-8000; lane 9 (K6M) is an SCFmet1-165 formulation containing 10 mM K phosphate, pH 6.0, and 5% mannitol; lane 10 (K6PM) is an SCFmet1-165 formulation containing 10 mM K phosphate, pH6.0, 5% mannitol, and 0.5% polyethylene glycol-8000; lane 11 (K6SuM) is an SCFmet1-165 formulation containing 10 mM K phosphate, pH 6.0, 0.5% sucrose and 4.5% mannitol; lane 12 (K6SuPM) is an SCFmet1-165 formulation containing 10 mM K phosphate, pH 6.0, 0.5% sucrose, 0.5% polyethylene glycol-8000 and 4.5% mannitol.

Figure 7:
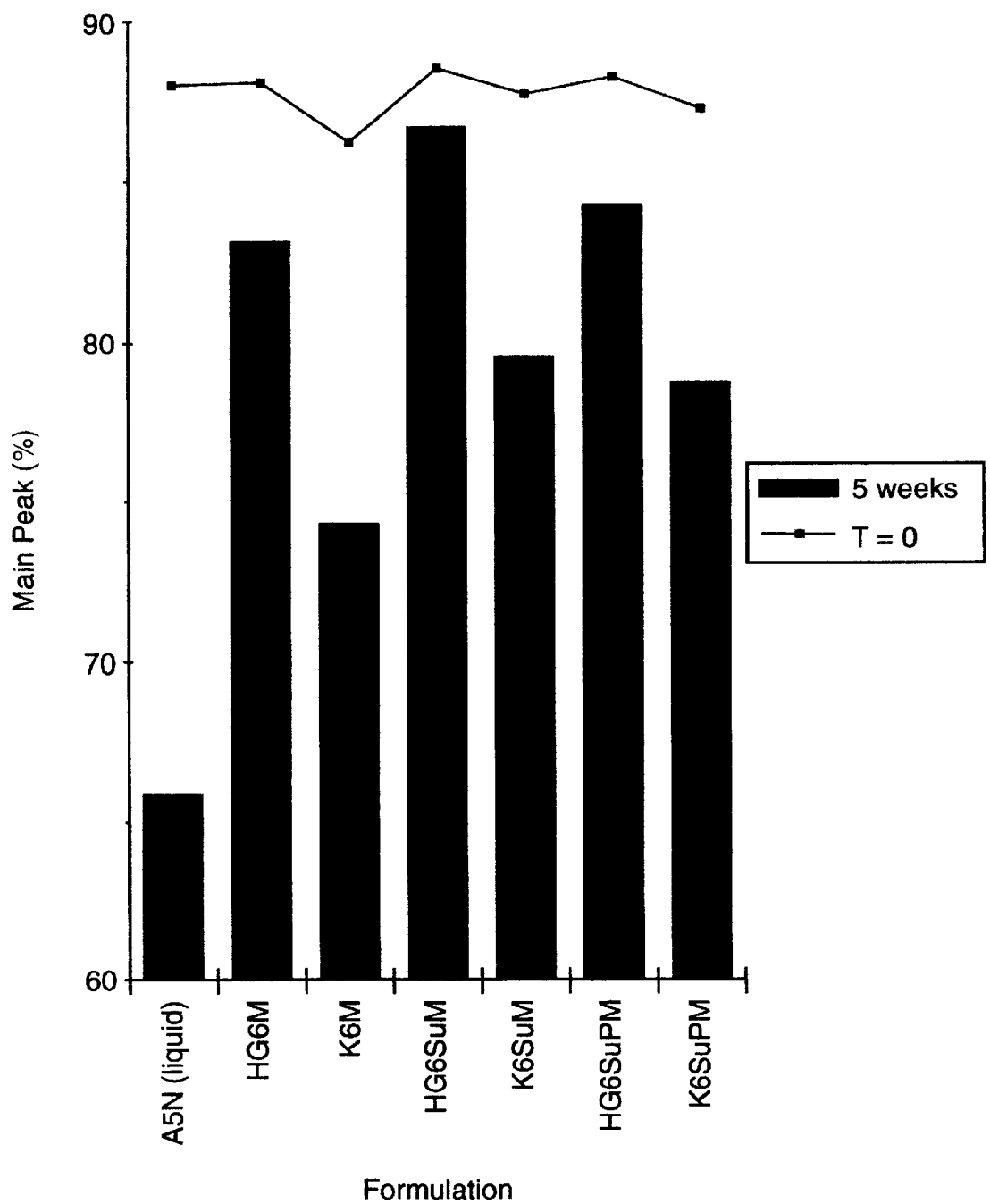

FIG. 7 is a bar graph illustrating the relative purity, in terms of species detectable by ion exchange-HPLC, of various SCF formulations as described in FIG. 6 above, after incubation for five weeks at 37° C.

DETAILED DESCRIPTION OF THE INVENTION

The present invention relates to SCF formulations with improved stability. One aspect of the present invention is lyophilized SCF formulations including histidine and/or glutamic acid. The lyophilized formulations may optionally include sucrose, and also optionally a bulking agent and an osmolarity regulating agent. In another aspect, the present invention relates to methods for production of such formulations.

While any SCF may be used herein, preferably those disclosed and taught in PCT WO91/05795 will be used, and most preferably human recombinant SCFmet1-165 as produced by *E. coli* will be used as the active ingredient.

The bulking agent is preferably mannitol, but others skilled in the art will recognized other agents suitable for forming a lyophilized "cake" with proper mass and osmolarity. Other agents include NaCl, glycine, polymers such as dextran, polyvinylpyrolidone, and carboxymethylcellulose, however, as indicated above, mannitol is preferred.

The SCF formulation will preferably include an amino acid selected from histidine and glutamic acid, and more preferably the formulation includes histidine, glutamic acid and sucrose. As will be demonstrated below, the most stable and therefore most preferable formulation includes lyophilized human recombinant SCFmet1-165, histidine, glutamic acid, sucrose, a bulking agent and an osmolarity regulating agent, which, as stated above, is most preferably mannitol. The pH is preferably adjusted to between pH 5.0 and pH 6.0, most preferably, pH 6.0

A preferred lyophilized formulation for SCF is 10 mM histidine, 5 mM glutamic acid, pH 6.0, 0.5% sucrose and 4.5% mannitol. Another preferred lyophilized formulation for SCF is 10 mM histidine, 5 mM glutamic acid, pH 6.0, with 5% mannitol. In addition, for all, the preferred active ingredient is SCFmet1-165, as indicated above, at a concentration of 0.25 –2.5 mg/mL, for reasons of greatest commercial practicability.

The present methods relate to the preparation of the present formulations. In one aspect, the present invention relates to a method for preparing a lyophilized SCF formulation comprised of the steps of:

(a) mixing said SCF in a buffer containing an amino acid selected from the group consisting of histidine and glutamic acid; and, (b) lyophilizing said SCF.

The present methods further comprise one or more of the following steps: adjusting the pH of said mixture to between pH 5.0 and pH 6.0 prior to lyophilization, adding sucrose to said mixture prior to lyophilizing, adding at least one agent selected from a bulking agent and an osmolarity regulating agent to said mixture prior to lyophilization. In the latter step, the agent may be mannitol, glycine, NaCl, or polymers, such as those listed on the previous page.

SCF may be used in the treatment of a variety of hematopoietic, neurological and reproduction related conditions. See WO 91/05795 which has been incorporated by reference, see also U.S. Ser. No. 07/982,255 which is also herein incorporated by reference. Thus, the present compositions and methods for manufacture of medicaments may be useful for the treatment of such conditions. Such conditions include but are not limited to the treatment of leucopenia, the treatment of thrombocytopenia, the treatment of anemia, enhancing engraftment of bone marrow during transplantation, enhancing bone marrow recovery in treatment of radiation, chemical or chemotherapeutic induced bone marrow aplasia or myelosuppression, acquired immune deficiency syndrome, and sensitizing cells to chemotherapy. Such uses and compositions also include providing treatment to a mammal suffering from nerve damage, infertility, or intestinal damage.

The present SCF formulations may also be used in vitro. For example, in a gene therapy setting, one may desire to transfect a hematopoietic cell with exogenous DNA, and culture said cell using the present SCF formulations. Thus, in yet another aspect the present invention involves a method for culturing hematopoietic cells in vitro comprised of:

(i) placing said cells in a suitable culture medium, said suitable culture medium containing SCF formulated according to the present invention, and (ii) providing suitable conditions for the growth of said hematopoietic cells.

More particularly, the present invention provides a method of transfecting hematopoietic cells with exogenous DNA comprising: (i) culturing said hematopoietic cells with SCF formulated according to the present invention, and (ii) transfecting said cultured cell with exogenous DNA. The hematopoietic cells may be, for example, bone marrow cells or peripheral blood progenitor cells.

In yet another aspect, the present invention provides a kit containing components for culturing bone marrow cells or peripheral blood progenitor cells comprised of:

(i) an SCF formulation of the present invention; and (ii) components suitable for preparing medium for culturing bone marrow cells or peripheral blood progenitor cells.

The uses or products herein may involve the administration or inclusion of at least one additional factor selected from among EPO, G-CSF, GM-CSF, M-CSF, CSF-1, IL-1, IL-2, IL-3, IL-4, IL-5, IL-6, IL-7, IL-8, IL-9, IL-10, IL-11, IL-12, IGF-1, LIF, interferon (such as α, β, gamma or consensus) neurotrophic factors (such as BDNF, NT-3, CTNF or noggin), other multi-potent growth factors, (such as stem cell proliferation factor, and totipotent stem cell factor), fibroblast growth factors (such as FGF), and analogs, fusion molecules or other derivatives of the above. For example, SCF in combination with G-CSF has been found to mobilize peripheral blood progenitor cells in vivo. Ex vivo, for example, SCF in combination with G-CSF, IL-3 and IL-6 has been found useful for expansion of peripheral blood cells.

The materials and methods used in the present examples are first described. Example 1 demonstrates that SCF formulations buffered with amino acids are more stable over time than SCF formulations in which pH is maintained with other compounds. Example 2 demonstrates that sucrose enhances the stability of SCF in amino and non-amino acid formulations. It also demonstrates, again, the increase in stability when amino acid buffers are used. Example 3 demonstrates the biological activity of the present formulations.

Materials and Methods

Preparation of Recombinant Human SCFMET1-165

SCFmet1-165 for the present formulation studies was produced in *E. coli* (K-12 strain). The nucleic acid sequence (SEQ ID No:1) used and amino acid sequence (SEQ ID No:2) is shown below. Following fermentation, the cell paste was lysed. The SCF was solubilized, refolded and oxidized, and purified by means of several chromatography steps. The apparent molecular weight of the protein is approximately 18,500.

```
ATGGAAGGTA TCTGCCGTAA CCGTGTTACT AACAACGTTA AAGACGTTAC
 M  E  G   I  C  R  N   R  V  T   N  N  V    K  D  V  T
TAAACTGGTT GCTAACCTGC CGAAAGACTA CATGATCACC CTGAAATACG
 K  L  V   A  N  L     P  K  D  Y   M  I  T    L  K  Y
TTCCGGGTAT GGACGTTCTG CCGTCTCACT GCTGGATCTC TGAAATGGTT
 V  P  G  M  D  V  L   P  S  H    C  W  I  S   E  M  V
GTTCAGCTGT CTGACTCTCT GACTGACCTG CTGGACAAAT TCTCTAACAT
 V  Q  L   S  D  S  L   T  D  L   L  D  K    F  S  N  I
CTCTGAAGGT CTGTCTAACT ACTCTATCAT CGACAAACTG GTTAACATCG
 S  E  G   L  S  N    Y  S  I  I    D  K  L    V  N  I
TTGACGACCT GGTTGAATGC GTTAAAGAAA ACTCTTCTAA AGACCTGAAA
 V  D  D  L   V  E  C   V  K  E   N  S  S  K    D  L  K
AAATCTTTCA AATCTCCGGA ACCGCGTCTG TTCACTCCGG AAGAATTCTT
 K  S  F   K  S  P  E    P  R  L    F  T  P   E  E  F  F
CCGTATCTTC AACCGTTCCA TCGACGCTTT CAAAGACTTC GTTGTTGCTT
```

```
    R    I    F         N    R    S         I    D    A    F         K    D    F         V    V    A

CCGAAACCTC     CGACTGCGTT     GTTTCCTCCA     CCCTGTCTCC     GGAAAAAGAC

S    E    T    S         D    C         V    V    S    S         T    L    S         P         E    K    D

TCCCGTGTTT     CGGTTACCAA     ACCGTTCATG     CTGCCGCCGG     TTGCTGCTAA

S    R    V         S    V    T    K         P    F    M         L    P    P         V    A    A    *
```

Preparation of Formulation Buffers

Formulation buffers were prepared from concentrated stock solutions. Buffers consisting of sodium succinate, potassium phosphate, glutamic acid (alone) or histidine (alone) were adjusted to the desired pH by addition of HCl or NaOH. Buffers consisting of combinations of amino acids (glutamic acid plus histidine) were prepared using the free acid or base form of the amino acid. The pH of the amino acid combination buffers was checked, but not adjusted after preparation.

Buffer Exchange. SCF was supplied in 10 mM Na acetate, pH 5.0, 140 mM NaCl. The protein was exchanged into the formulation buffers by dialysis at 4° C. using SpectraPor 7 dialysis membranes, molecular weight cut-off approximately 3,500. Each sample was dialyzed against 3 changes of the formulation buffer, where each change of buffer was at least 100×the volume of the sample being formulated. PEG-8000 was added from a concentrated stock solution following dialysis. Alternatively, buffer exchange could be performed by diafiltration, desalting over a GPC column, or any other appropriate method.

Following buffer exchange, the SCF concentration was determined by absorbence at 280 nm and adjusted by dilution to the desired value. SCF concentration can range from 0.25 mg/mL or less to 12.5 mg/mL or greater. (The SCF concentration is specified for each example below). In a laminar flow hood, samples were sterile filtered using 0.22 micron Gelman Acrodisc syringe filters and filled into 3 cc Type I glass vials. Lyophilization stoppers were positioned over the vials in the laminar flow hood.

Lyophilization. Samples were loaded into a VirTis Genesis 12 EL (VirTis, Gardiner, N.Y. 12526) lyophilizer that was pre-cooled to a chamber temperature of approximately 4° C. Samples were frozen rapidly (about 1 degree C./minute to −50° C.) and held at that temperature for at least 2 hours. In an optional step to crystallize mannitol, the shelf temperature was raised to −25° C. for 2–3 hours, and then cooled to −50° C. at a rate of 10 degrees C./hour. After an additional hold of at least 2 hours, a vacuum of approximately 100 mTorr was applied. The shelf temperature was raised to a temperature ranging from −45° C. to −10° C. for primary drying. (Primary drying temperature is specified for each of the examples below). Primary drying was continued for 24–48 hours. The shelf temperature was then raised to +20° C. to +25° C. for secondary drying and vacuum was lowered as far as possible (typically about 25 mTorr). Secondary drying was performed for 24–72 hours. At the conclusion of secondary drying, the samples were stoppered under vacuum (</=25 mTorr) and vials removed from the freeze dryer. In order to perform accelerated stability studies, some samples were transferred to incubators for storage. Other samples were transferred to a −70° C. freezer to serve as controls. The bulk of the vials were stored at 4° C. At the time of analysis, samples were reconstituted with sterile WFI to the desired concentration.

SDS-PAGE. SDS-PAGE was performed by standard methods (Laemmli, Nature 227: 680–685 (1970)). Single concentration 15% polyacrylamide gels were used for the separation. For loading, 7.5 μg of material was used per lane. Gels were stained with Coomassie Blue and scanned using a Molecular Dynamics Personal Densitometer. After scanning, the gels were either dried as is or re-stained with silver stain.

Reverse-Phase (RP)-HPLC. RP-HPLC was performed on a Waters 625 LC System using a 5 micron C4 column from Vydac, pore size 300 A. Protein was injected onto a column equilibrated with 45.6% acetonitrile, 0.1% trifluoroacetic acid (TFA) and eluted with a linear gradient from 45.6 to 64.6% acetonitrile, 0.1% TFA. Protein peaks were monitored by absorbence at 220 nm.

Size Exclusion (SEC)-HPLC. SEC-HPLC was performed on a Waters 625 LC System using a Phenomenox BioSep SEC-S3000 column. The elution buffer was 100 mM phosphate, pH 6.9. Protein was monitored by absorbence at 280 nm.

Ion Exchange (IEX)-HPLC. IEX-HPLC was performed on a Waters 625 LC System using a TSK Progel 5P-5PW column at room temperature. Samples were diluted 6×in 20 mM sodium acetate, pH 4.8 buffer and applied to a column equilibrated in the same buffer. SCF was eluted using a linear gradient of $Na_2SO_4$ 0–0.5M. Protein was monitored by absorbence at 230 nm.

Biological Activity. Bioactivity was tested using the growth factor dependent human megakaryocyte cell line UT-7. Upon administration of SCF, a proportion of the cells re-enter the cell cycle and progress to S-phase (DNA sysnthesis). The present assay is based on this response as determined by $^3$H-thymidine uptake. UT-7 cells were washed to remove exogenous growth factor, and plated in the presence of various SCF samples as described in Example 3. After three days, a six hour pulse of $^3$H-thymidine was administered. Incorporation into DNA was measured by washing, harvesting and counting the radioactivity of the cells deposited on glass fiber filters. Activity as measured in units of mass of test samples was determined by comparison to a standard curve.

EXAMPLE 1

This Example demonstrates improvement in SCF stability in formulations buffered with amino acids. It also demonstrates further improvements when combinations of amino acids were used. In this Example, formulations with no amino acids were compared to formulations using amino acids, at two different pH's:

| pH 5.0 | pH 6.0 |
|---|---|
| S5M (10 mM sodium succinate, pH 5.0, 5% mannitol) | |
| G5M (10 mM glutamic acid, pH 5.0, 5% mannitol) | H6M (10 mM histidine pH 6.0, 5% mannitol) |
| GH5M (10 mM glutamic acid, 8.35 mM histidine pH 5.0, 5% mannitol) | HG6M (10 mM histidine, 5 mM glutamic acid, pH 6.0, 5% mannitol) |

The SCF concentration was 6.0 mg/mL for all samples. No acid or base was added to adjust the pH of formulations containing combinations of amino acids; thus, these samples contain no salt. The pH of the other formulations was adjusted by titration with small amounts of NaOH or HCl. All formulations were lyophilized under the same conditions; the primary drying temperature for this study was −25° C. For comparison, a liquid formulation (also 6.0 mg/mL SCF) was shown. The liquid formulation (A5N) was 10 mM sodium acetate, pH 5.0, 140 mM NaCl.

The samples were incubated at a high temperature, 45° C., for at least four weeks. Some samples were maintained at 45° C. for twelve weeks. At the end of the time period, the samples were analyzed for degree of stability.

The results are illustrated in FIGS. 1, 2, and 3, which show (1) the formulations containing amino acids were more stable over time than those buffered without amino acids; (2) the formulations containing amino acids at pH 6.0 performed better than those at pH 5.0; (3) the formulations containing a combination of the amino acids histidine and glutamic acid, at pH 6.0 performed best, in that they show the lowest rate of increase of SCF species differing from the starting material (fragments, aggregates, etc.) as determined by various analytical methods.

FIG. 1 is a bar graph illustrating the degree of cross-linked SCF products (i.e., SCF oligomers, a degradation product) after incubation at an accelerated temperature (45° C.), as determined by SDS-PAGE, as described above. As can be seen, the lyophilized formulations containing amino acids as buffers contained fewer crosslinked dimers than the formulation containing sodium succinate as a buffer (S5M). Generally, fewer dimers were observed in the formulations at pH 6.0 (H6M and HG6M) than comparable formulations at pH 5.0 (G5M and GH5M).

FIG. 2 is a bar graph illustrating the degree of non-covalent aggregation found in the various formulations, as determined by size exclusion chromatography, as described above. As can be seen, the formulation having succinate pH 5.0 buffer has the highest percent aggregation (greater than 3%), and again, consistent with the results illustrated in FIG. 1, the SCF formulation buffered with histidine and glutamic acid at pH 6.0 (HG6M) contained the lowest percent aggregation (less than 1%).

FIG. 3 is a bar graph illustrating the percent purity (i.e., the percent of main peak as determined by reverse phase HPLC as described above) of the various SCF formulations. This measurement was taken after incubation at high temperature for 12 weeks. This graph illustrates that the SCF formulation HG6M, containing histidine, glutamic acid and mannitol at pH 6.0, had the highest percent purity, of over 90% (as determined by these methods) of the samples tested. The second highest was also for an amino acid combination buffer formulation, GH5M, at pH 5.0, which also had a purity of over 90%. Note that the liquid control (A5N) had a percent purity of between 60 and 70%. RP-HPLC degradation, a major pathway of solution instability, is substantially reduced using the present compositions and methods.

EXAMPLE 2

This Example shows, in two steps, that sucrose improves stability of the formulations tested. The first study shows that sucrose improves the stability of SCF formulations buffered in non-amino acid containing buffers. Additionally, in the non-amino acid containing buffers containing sucrose, polyethylene glycol was shown to also contribute to stability. This study also shows that an SCF formulation using the amino acid buffers histidine and glutamic acid is more stable than the non-amino acid buffered formulations, even when the latter contains additional stabilizers.

The second study demonstrates that sucrose also enhances stability of the amino-acid buffered formulations. Polyethylene glycol-8000 was shown to have no effect, however, on the stability of these formulations.

Study 1. Here, all formulations were at pH 6.0. Formulations buffered by amino acids were compared to formulations buffered by potassium phosphate, +/−sucrose and +/−polyethylene glycol 8000:

| Amino acid buffered | Potassium Phosphate Buffered |
|---|---|
| HG6M (10 mM histidine, 5 mM glutamic acid, pH 6.0, 5% mannitol) | K6M (10 mM potassium phosphate, pH 6.0, 5% mannitol) |
| | K6SuM (10 mM potassium phosphate, pH 6.0, 0.5% sucrose, 4.5% mannitol) |
| | K6SuPM (10 mM potassium phosphate, pH 6.0, 0.5% sucrose, 0.5% PEG-8000, 4.5% mannitol) |

All formulations used SCFmet1-165 at 1.5 mg/mL. No acid or base was added to adjust the pH of the formulation buffered with the combination of amino acids. All formulations were lyophilized under the 10 conditions as described above, the primary drying temperature being −25° C. A liquid formulation (also 1.5 mg/mL SCFmet1-165) was used for comparison, and it contained 10 mM sodium acetate, pH 5.0, 140 mM NaCl.

FIG. 4 shows a silver-stained SDS gel of 15 samples after 4 weeks incubation at 45° C. Among the potassium phosphate buffered formulations, K6SuPM shows the smallest high molecular weight band, indicating the lowest degree of cross-linked (i.e., covalently dimerized) SCF. This indicates that for the phosphate buffered formulations, sucrose and polyethylene glycol contribute to stability. What FIG. 4 also shows, however, is that the formulation containing amino acid buffer has the least material at the high molecular weight, indicating that the histidine/glutamic acid formulation is even more stable that the potassium phosphate/sucrose/polyethylene glycol formulation.

FIG. 5 shows a size exclusion-HPLC (as 5 described above) chromatogram of the above samples (HG6M, K6SuM, K6SuPM, and the liquid control, A5N. The samples were incubated for six weeks at 45° C. As can be seen, the HG6M displays one major peak, and one minor peak (containing aggregate). In substantial contrast, the potassium phosphate buffered formulations contained several peaks.

Study 2. In this study, sucrose and polyethylene glycol were added to the amino acid buffered formulations and compared to potassium phosphate buffered formulations:

| Amino Acid Buffered | Potassium Phosphate Buffered |
|---|---|
| HG6M (10 mM histidine, 5 mM glutamic acid, pH 6.0, 5% mannitol) | K6M (10 mM K phosphate, pH 6.0, 5% mannitol) |
| HG6PM (10 mM histidine, 5 mM glutamic acid, pH 6.0, 0.5% PEG-8000, 5% mannitol) | K6PM (10 mM K phosphate, pH 6.0, 0.5% PEG-8000, 5% mannitol) |
| HG6SuM (10 mM histidine, 5 mM glutamic acid, pH 6.0, 0.5% sucrose, 4.5% mannitol) | K6SuM (10 mM K phosphate, pH 6.0, 0.5% sucrose, 4.5% mannitol) |
| HG6SuPM (10 mM histidine, 5 mM glutamic acid, pH 6.0, 0.5% sucrose, 0.5% PEG-8000, 4.5% mannitol) | K6SuPM (10 mM K phosphate, pH 6.0, 0.5% sucrose, 0.5% PEG-8000, 4.5% mannitol) |

Similar to Study 1 in this Example, above, all formulations used SCFmet1-165 at 1.5 mg/mL. No acid or base was added to adjust the pH of the formulations buffered with the combination of amino acids. All formulations were lyophilized under the conditions as described above, the primary drying temperature being −35° C. A liquid formulation (also 1.5 mg/mL SCFmet1-165) was used for comparison, and it contained 10 mM sodium acetate, pH 5.0, 140 mM NaCl.

FIG. 6 shows a silver-stained SDS gel of samples after 5 weeks of incubation at an elevated temperature of 45° C. At the identical pH (pH 6.0), the formulations buffered with the combination of histidine and glutamic acid show much less crosslinking than the equivalent formulations buffered with potassium phosphate. The addition of 0.5% sucrose significantly improves the stability of the histidine/glutamic acid buffered as well as the phosphate buffered formulations. The addition of polyethylene glycol 8000 had no effect on the degree of crosslinking seen; this may have been due to the lower temperature of primary drying (−35° C. here vs. −25° C. with the Study 1 samples).

FIG. 7 shows a comparison of the same formulations by ion-exchange chromatography. Again, the histidine/glutamic acid buffered formulations show greater stability under the accelerated incubation conditions than the equivalent phosphate buffered formulations. Incorporation of sucrose (0.5%) improves the stability of both the amino acid and phosphate buffered formulations.

EXAMPLE 3

Biological Activity. All samples in the amino acid containing buffers demonstrated biological activity similar to SCF in solution. The above samples from Example 1 were tested for biological activity after 4 weeks (at 2–8° C.) and again at 1 year (stored at 2–8° C.), using the UT-7 bioassay, as described above. The table below shows the concentration of active material of various samples.

As can be seen, the biological activities among all samples are comparable to that of the starting material.

| Sample | Concentration (mg/ml) 4 weeks | Concentration (mg/ml) 1 year |
|---|---|---|
| Starting material, stored −80° C. | 6.2 | 4.3 |
| A5N | 6.5 | 3.9 |
| S5M | 6.5 | 3.9 |
| G5M | 5.7 | 4.4 |
| GH5M | 6.5 | 4.6 |
| H6M | 5.7 | 6.2 |
| HG6M | 6.0 | 5.7 |

While the present invention has been described in terms of preferred embodiments, it is understood that variations and modifications will occur to those skilled in the art. Therefore, it is intended that the appended claims cover all such equivalent variations which come within the scope of the invention as claimed.

What is claimed is:

1. A lyophilized stem cell factor ("SCF") formulation containing histidine.

2. A lyophilized SCF formulation containing glutamic acid.

3. A lyophilized SCF formulation of claims 1 or 2 wherein said formulation contains sucrose.

4. A lyophilized SCF formulation of claims 1 or 2 wherein said formulation contains mannitol.

5. A lyophilized SCF formulation containing histidine and glutamic acid.

6. A lyophilized SCF formulation of claim 5 further containing sucrose.

7. A lyophilized SCF formulation of claim 5 further containing mannitol.

8. A lyophilized SCF formulation containing 10 mM histidine, 5 mM glutamic acid and optionally 0.5% sucrose, and 4.5% mannitol.

9. A method for preparing a lyophilized SCF formulation comprised of the steps of:
    (a) mixing said SCF in a buffer containing an amino acid or amino acids selected from the group consisting of histidine and glutamic acid; and,
    (b) lyophilizing said SCF.

10. A method of claim 9 wherein the pH of said buffer is between pH 5.0 and pH 6.0 prior to lyophilization.

11. A method of claim 10 further comprising adding sucrose to said formulation prior to lyophilizing.

12. A method of claim 11 further comprising adding at least one agent selected from a bulking agent and an osmolarity regulating agent to said formulation prior to lyophilization.

13. A method of claim 12 wherein said agent is mannitol.

\* \* \* \* \*